United States Patent [19]

Fuchs et al.

[11] Patent Number: 5,246,577

[45] Date of Patent: Sep. 21, 1993

[54] APPARATUS FOR EFFECTING CAPILLARY ELECTROPHORESIS

[75] Inventors: Martin Fuchs, Uxbridge; Michael Merion, Upton, both of Mass.

[73] Assignee: Millipore Corporation, Bedford, Mass.

[21] Appl. No.: 911,997

[22] Filed: Jul. 10, 1992

Related U.S. Application Data

[63] Continuation of Ser. No. 530,121, May 29, 1990, abandoned.

[51] Int. Cl.$^5$ .............................................. B01D 15/08
[52] U.S. Cl. .................................. 210/198.2; 210/635; 210/656; 204/180.1; 204/182.8; 204/299 R
[58] Field of Search ............. 204/180.1, 182.8, 299 R; 210/635, 656, 198.2

[56] References Cited

U.S. PATENT DOCUMENTS

| | | | |
|---|---|---|---|
| 2,678,300 | 5/1954 | Sturtevant | 204/299 R |
| 2,989,457 | 6/1961 | Oss | 204/299 R |
| 3,298,527 | 1/1967 | Wright | 210/198.2 |
| 3,384,564 | 5/1968 | Ornstein | 204/299 R |
| 3,640,813 | 2/1972 | Nerenberg | 210/198.2 |
| 3,782,078 | 1/1974 | Jerpe | 210/198.2 |
| 3,791,522 | 2/1974 | Eisenbeiss | 210/198.2 |
| 3,795,600 | 3/1974 | Allington | 204/299 R |
| 3,847,785 | 11/1974 | Allington | 204/299 R |
| 3,902,849 | 9/1975 | Barak | 210/198.2 |
| 3,969,218 | 7/1976 | Scott | 204/299 R |
| 4,107,041 | 8/1978 | Karlson | 210/198.2 |
| 4,211,658 | 7/1980 | McDonald | 210/198.2 |
| 4,238,327 | 12/1980 | Libudry | 210/198.2 |
| 4,290,855 | 9/1981 | O'Farrell | 204/299 R |
| 4,323,439 | 4/1982 | O'Farrell | 204/182.8 |
| 4,459,198 | 7/1984 | Mizuno | 204/299 R |
| 4,483,773 | 11/1984 | Yang | 210/656 |
| 4,551,249 | 11/1985 | Shackelford | 210/198.2 |
| 4,551,251 | 11/1985 | Kolobow | 210/198.2 |
| 4,554,071 | 11/1985 | Ruijten | 210/198.2 |
| 4,565,632 | 1/1986 | Hatch | 210/198.2 |
| 4,636,316 | 1/1987 | Harris | 210/198.2 |
| 4,676,897 | 6/1987 | Kuze | 204/299 R |
| 4,708,782 | 11/1987 | Andresen | 210/198.2 |
| 4,793,920 | 12/1988 | Cortes | 210/198.2 |
| 4,806,238 | 2/1989 | Sattler | 210/198.2 |
| 4,859,301 | 8/1989 | Brenner | 204/299 R |

OTHER PUBLICATIONS

Synder, Introduction to Modern Liquid Chromatography, John Wiley and Sons Inc., New York, 1979, pp. 720-731.

Jorgenson, "High-Resolution Separations Based on Electrophoresis and Electroosmosis", Journal of Chromatography, 218 (1981) pp. 209-216.

Aebersold and Morrison at the High Performance Capillary Electrophoresis Symposium in Jan. 1990 p. 43.

*Primary Examiner*—Ernest G. Therkorn
*Attorney, Agent, or Firm*—Andrew T. Karnakis; Paul J. Cook

[57] ABSTRACT

An apparatus is provided for concentrating a solute sample which can be subsequently released for analysis by capillary electrophoresis. The apparatus comprises a tube containing a short length of packed particles or gel adapted to retain sample solutes which particles are retained in the tube by tube constrictions or porous plugs. The tube includes an inlet for introducing a sample into the tube and an outlet for introducing the retained sample into a capillary electrophoresis tube.

7 Claims, 5 Drawing Sheets

APPARATUS FOR EFFECTING CAPILLARY ELECTROPHORESIS

This is a continuation of co-pending application Ser. No. 07/530,121 filed on May 29, 1990 now abandoned.

BACKGROUND OF THE INVENTION

This invention relates to a method and apparatus for performing capillary electrophoresis. More particularly, this invention relates to an improved method and apparatus for capillary electrophoresis that permits concentration of solutes from a solution prior to separating the solutes by capillary electrophoresis.

Capillary electrophoresis (CE) is an efficient analytical separation technique for analysis of minute amounts of sample. CE separations are performed in a narrow diameter capillary tube, which is filled with an electrically conductive medium termed the "carrier electrolyte." An electric field is applied between the two ends of the capillary tube, and species in the sample move from one electrode toward the other electrode at a rate which is dependent on the electrophoretic mobility of each species as well as on the rate of fluid movement in the tube. CE may be performed using gels or liquids, such as buffers, in the capillary. In one liquid mode, known as free zone electrophoresis, separations are based on differences in the free solution mobility of sample species. In another liquid made, micelles are used to effect separations based on differences in hydrophobicity. This is known as Micellar Electrokinetic Capillary Chromatography (MECC).

CE is advantageous for several reasons. These include fast separation speed, high resolution and small sample size. For example, separation speeds using CE can be 10 to 20 times faster than conventional gel electrophoresis, and no post-run staining is necessary. In part, high resolution can be obtained through the use of high voltages because of the rapid dissipation of heat by the capillary. Further, band broadening is minimized due to the narrow capillary inner diameter In free-zone electrophoresis, the phenomenon of electroosmosis, or electroosmotic flow (EOF) occurs. This is a bulk flow of liquid which affects all of the sample molecules regardless of charge. Under certain conditions EOF can contribute to improved resolution and separation speed in free-zone CE.

In order to achieve the high resolution that CE is capable of, it is necessary that the sample be confined to a narrow starting zone when the electrophoretic process begins. This limits the volume of sample that can be introduced into the capillary to a very small fraction of the total capillary volume. Further, the lowest concentration of material that can be detected in CE by ultraviolet and visible absorbance detection is severely limited by the small inner diameter of the capillary, since absorbance detection is generally carried out with a beam of radiation that is transverse to the axis of the capillary. These facts, taken together, mean that CE has not been able to analyze samples at concentrations as low as those that can be analyzed by other techniques such as liquid chromatography. One approach to overcome this limitation has been described by several investigators. This approach involves dissolving the sample in a buffer or electrolyte having an ionic strength substantially lower than the carrier electrolyte used to carry out the electrophoretic separation. The sample so dissolved is introduced into the capillary in the normal fashion although a larger sample volume is now permitted. When the electric field is applied to begin the electrophoretic separation, the field strength in the sample zone will be higher than in the surrounding carrier electrolyte because the ionic strength and hence the conductivity is lower in the sample zone. As a result of the higher field strength in the sample zone, the ions in the sample will migrate at a higher speed than ions in the carrier electrolyte. Thus the sample ions will tend to pile up at the interface of the low conductivity sample zone and the carrier electrolyte because they will slow down once they enter the carrier electrolyte. This process effectively produces a narrow sample zone and has allowed an improvement of perhaps a factor of five in the lowest concentration of sample that can be analyzed.

A technique for preconcentrating a sample prior to electrophoretic separation was reported by Aebersold and Morrison at the High Performance Capillary Electrophoresis Symposium in January 1990. The inner surface of a short piece of a capillary tubing was coated with an adsorptive coating. This tube was then butted up against the end of an uncoated capillary tube. This arrangement permitted a large volume of sample (which would normally have caused severely broadened peaks) to be injected into the coated length of tube and then into the uncoated tube. The sample molecules adsorbed on the coating while the solvent passed through the tube and was washed out of the capillary tube with electrolyte. A small volume of organic solvent was then introduced into the butted capillary tubes. This solvent caused the sample molecules to desorb from the coating so that they entered the uncoated tube in concentrated form. Because the organic solvent had lower conductivity than the carrier electrolyte, the previously mentioned zone narrowing then occurred. With both ends of the capillary tube in electrolyte, capillary electrophoretic separation was then performed in normal fashion. It was reported that this preconcentration step allows the use of CE with samples 5 to 10 times lower in concentration than was previously possible with CE.

Packed capillary columns have been used in liquid chromatography to effect sample separations. Such columns have been constructed in various ways. One way of making such a column is disclosed by Jorgenson, et al in Journal of Chromatography, Vol. 218 (1981) pgs. 209–216. The column is formed by filling one end of a capillary tube with a particulate packing. The filled end then is heated in a flame to sinter the packing to form a porous frit. A slurry of chromatographic separation particles is introduced into the end of the capillary opposite to the fritted end until the capillary is filled with these particles. A second frit then is formed in the open end of the capillary in the same manner as was the first frit.

As disclosed in U.S. Pat. No. 4,793,920 to Cortes et al, a packed silica capillary chromatography column is produced by casting a plug of ceramic material in one end of the capillary to form a porous plug which is fused such as with heat. The chromatographic packing then is introduced into the remainder of the tube. U.S. Pat. No. 4,483,773 to Yang also discloses a means for forming a Plug and chromatographic packing within a capillary chromatographic column.

It would be desirable to provide a means whereby dilute sample solution can be analyzed by CE at concentrations far lower than can be analyzed by presently available CE processes.

SUMMARY OF THE INVENTION

The present invention provides a CE pretreatment process and apparatus which permits the use of CE to analyze samples having a concentration of at least one order of magnitude less than can be analyzed by presently available CE processes. In accordance with the invention, a sample concentration means is provided wherein a solute sample is retained by a confined solid or gel packing in a tube while the solvent passes through the packing. The particles are confined within a tube such as a capillary tube by mechanical means such as tube constrictions or porous plugs positioned at both ends of the packed concentrating solid particles or gel. The concentrating particles or gel have a higher adsorptive capacity and longer useful life as compared to a wall coating of adsorptive composition. The sample concentration means of this invention is formed either integrally with a capillary tube useful in CE or in a separate tube which can be used in conjunction with a capillary tube useful in CE. In one embodiment, a constriction is formed in the tube, packing material is introduced into the tube to the constriction and a second constriction is formed in the tube at a second end of the packing thereby to confine the packing within the tube. In a second embodiment, low temperature heat fusible particles are introduced into the tube and heated to form a porous plug. Packing material is then introduced into the tube to the plug and a second porous plug is formed in the same manner at a second end of the packing thereby to confine the packing within the tube.

DESCRIPTION OF SPECIFIC EMBODIMENTS

Figure 1:
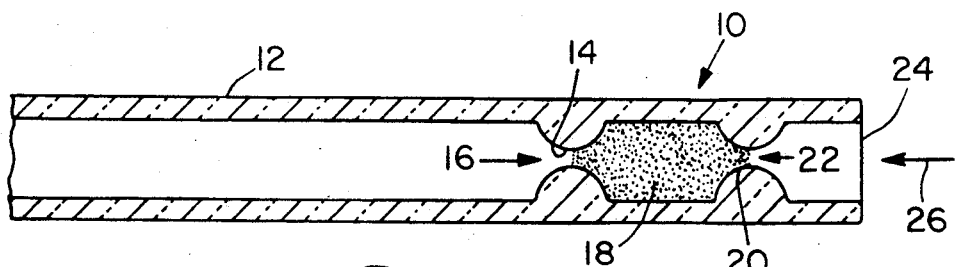
FIG. 1 is a cross-sectional view of a one piece embodiment of this invention.

The sample concentration column of this invention can be formed as an integral part of a capillary tube used for electrophoresis or from a separate tube having an inner diameter larger or smaller than the capillary tube used for electrophoresis, but which can be used in conjunction with the capillary tube used in capillary electrophoresis. The term "capillary tube" as used herein means a tube having an inner diameter between about 1 and 500 micrometers.

The sample concentration tube contains a solid particulate or gel packing capable of retaining a sample such as by adsorption, absorption or chemical interaction and which is capable of subsequently releasing the sample when contacted with a suitable solvent.

Representative suitable packing particles include silica particles, alumina particles, or zirconia particles with hydrophobic surface coatings such as C18 compound, C8 compound, or C4 compound; ion exchange materials such as diethyl amino ethyl (DEAE), sulfo propyl (SP) or quaternary amino ethyl (QAE); or affinity coated particles such as protein, antibodies, or azo dyes. Alternatively, the packing can comprise a gel packing that can be formed in the tube in situ such as polyacrylamide, agarose, cellulose, and polyethylene oxides.

The solid particulate or gel packing is held in place within the tube by porous plugs or constrictions. Representative suitable particulate materials which can be used to form a porous plug include low melting point glass particles such as borosilicate glass particles which can be formed into a frit by sintering in situ in the tube or a porous ceramic plug which is preformed and then inserted into the tube. Additionally, other mechanical means which allow liquid flow therethrough, but which retains the packing can be utilized as the porous plug.

When forming a sample concentration column wherein the packing material is held in place with constrictions in the tubes, the constrictions are formed by concentrating thermal energy along a short length of the tube in the area where a constriction is desired. The energy is sufficient to cause that portion of the tube to flow thereby to form a smaller inner diameter within the tube. A convenient means for forming a constriction is to rotate the tube within an electric arc formed between electrodes so that the energy applied to the tube is evenly applied about its circumference. After one constriction is formed and the tube is cooled to solidify it, the particulate packing is introduced into the tube to the constriction. A second constriction then is formed in the same manner at the opposite end of the packing. In an alternative embodiment a portion of the tube is filled with particles having a lower melting point than the tube and which are capable of forming a porous plug when fused. The particles are fused by heating and cooled to form the plug. The particles which interact with the sample are introduced into the tube to the porous plug and a second porous plug is formed in the same manner at the second end of the concentrating particles in a capillary tube. The concentrating particles generally have a diameter between about 1 um and 50 um, and the packed length is about 0.5 to 10 mm.

Referring to FIG. 1, a packed concentration column 10 is formed integrally with a capillary tube 12 useful in CE. The column 10 is formed by first forming a constriction 14 such that the diameter of opening 16 is between about 1 and 50 um. The packing 18 then is introduced into tube 10 as a slurry by any suitable means such as drawing the slurry in with a vacuum or pumping the slurry in with pressure. A second constriction 20 then is formed within the tube 10 such as in the manner described above such that the diameter of opening 22 is between about 1 and 50 um. In use, the sample to be treated is introduced in a solvent through tube entrance 24 as shown by arrow 26 and the sample solutes are retained in packing 18 while the solvent passes into capillary tube 12. A small volume (1–10 nl) of a second solvent is then introduced into entrance 24 to release the solutes from the packing and transport them into the capillary tube 12 where they are separated by CE in a manner more fully described below. The conductivity of the second solvent can be lower than the conductivity of the carrier electrolyte. This will effectively narrow the sample zone in the manner previously described. Optionally, an electrolyte can be introduced into the capillary tube before introducing the second solvent therein so that the sample solvent is flushed out and electrolyte is present in the entire capillary in order to conduct capillary electrophoresis.

Figure 2:
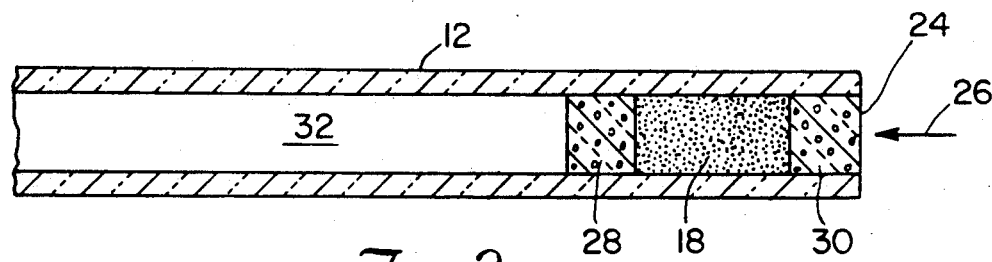
FIG. 2 is a cross sectional view of an alternative one piece embodiment of this invention.

Referring to FIG. 2, where like numbers to those in FIG. 1 refer to like elements, low melting particles 5 which can be converted to a porous plug by heating are introduced into capillary tube 12 by any convenient means such as a tamping wire (not shown) having a diameter equal to or less than that of the inner diameter of the capillary tube 12. The low melting particles are heated by exposing the tube 12 to a heating source to melt the particles but not the tube 12 followed by cooling to form the porous plug 28. A packing of concentrating particles 18 capable of retaining a solute then is introduced into tube 12 into contact with porous plug 28. The concentrating particles can be conveniently introduced into the tube as a slurry. A second porous plug 30 then is formed in the same manner as plug 28. The sample concentration packing 18 then is utilized by introducing a solvent containing the sample solute(s) into opening 24 so that solvent passes through the plugs 28 and 30 as well as packing 18 while sample solute(s) is retained by packing 18. A small volume (1–10 nl) of a second solvent which releases the retained sample solute(s) then is passed through the plugs 28 and 30 as well as packing 18 into the interior 32 of capillary 12 for analysis by CE. The packing 18 is retained between the plugs 28 and 30 during use.

Figure 3:
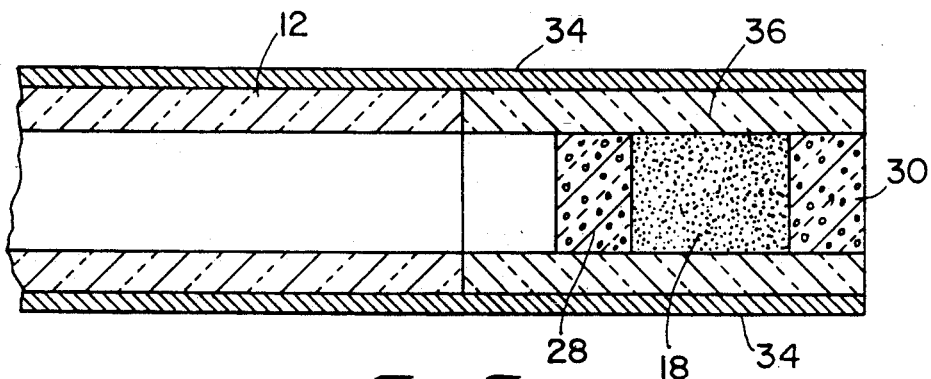
FIG. 3 is a cross sectional view of a two piece embodiment of this invention.

Referring to FIG. 3, a two piece construction is shown housed within a sleeve 34 comprising a capillary tube 12 and a capillary sample concentration tube 36 having essentially the same inner diameter as capillary tube 12. The interior of tube 36 contains two porous plugs 28 and 30 as well as particulate packing 28 as is discussed above with reference to FIG. 2 and is used in the same manner. The advantage of the two piece construction is that when the utility of the sample concentration tube 36 ceases, it can be removed from the sleeve 34 and discarded while the capillary tube 12 is retained. Similarly, the capillary tube can be discarded separately when its utility ceases.

Figure 4:
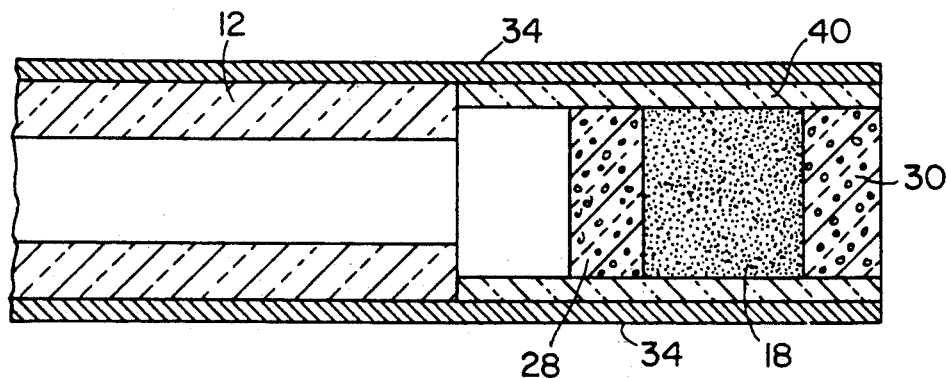
FIG. 4 is a cross sectional view of an alternative how piece embodiment of this invention.

An alternative two piece construction is shown in FIG. 4 wherein the sample concentration tube 40 has a larger inner diameter than the capillary tube 12 and wherein both tubes 40 and 12 are retained within sleeve 34. It is to be understood that the outer diameter of tube 40 can be larger than the outer diameter of tube 12 with sleeve 34 is shaped accordingly so that the tubes 12 and 40 contact each other and so that fluid flow can be effected between tubes 40 and 12. The sample concentration tube 40 contains porous plugs 28 and 30 as well as particulate packing 18 and is formed and used in the same manner as described above. This embodiment has the advantage that a large solute sample retaining capacity is obtained for a given length of sample concentration tube and that either the capillary tube or the sample concentration tube can be selectively discarded in the manner described above. The embodiments of FIGS. 3 and 4 can utilize tube constrictions as shown in FIG. 1 rather than the porous plugs as shown. Likewise, the sample concentration tube 40 can have a smaller, rather than larger, inner diameter than the capillary tube 12.

Figure 5:
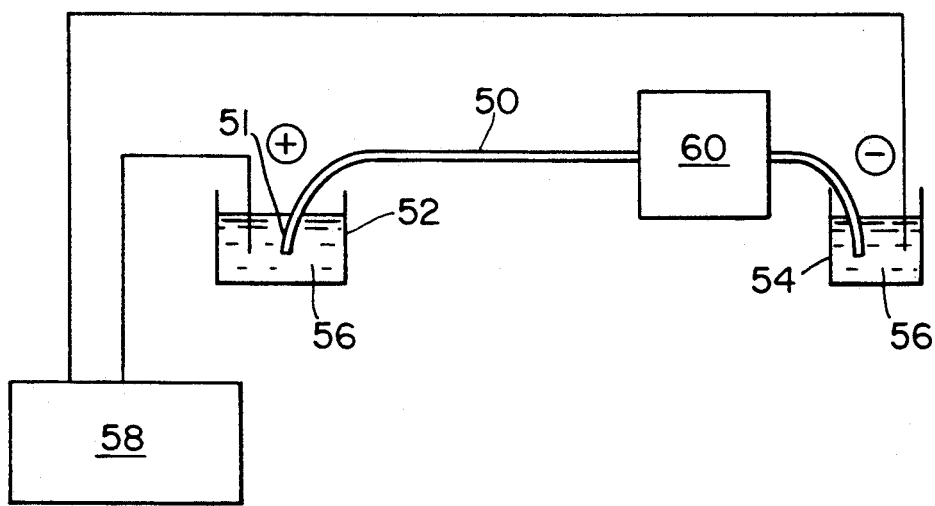
FIG. 5 is a schematic view of a capillary electrophoresis process utilizing this invention.

Referring to FIG. 5, a basic system that can be used in free zone capillary electrophoresis (CE), capillary gel electrophoresis or micellar electrokinetic capillary chromatography (MECC) is shown. In capillary gel electrophoresis, the capillary tube is filled with an electrically conductive gel rather than liquid electrolyte as in CE. For all of the above mechanisms, as shown in FIG. 5, a tube arrangement 50, as shown in more detail in FIGS. 1–4, is positioned between two reservoirs 52 and 54, each of which contains an electrolyte 56. In a first step, reservoir 52 is replaced with a reservoir containing sample and a voltage from power supply 58 is applied between the sample reservoir and reservoir 54. The sample is passed through the forward portion 51 of tube 50 which contains the sample concentration packing described above. After a volume of sample has been passed through the forward portion 51 of the tube 50 and solutes retained within packed portion, reservoir 52 is replaced with a reservoir containing a solvent capable of eluting the retained sample from the packing. This solvent is introduced into the tube 50 by applying a potential, typically between about 5 and 30 Kv, between the solvent reservoir and reservoir 54 for brief periods of time (1–10 sec.). Finally, the solvent reservoir is replaced with electrolyte reservoir 52, and a potential is applied between reservoir 52 and reservoir 54 to perform the separation. The eluted sample passes through the capillary tube 50, past detector 60 and into reservoir 54. The detector can be any detector capable of analyzing the sample such as a UV absorbance detector, a fluorescence detector, a conductivity detector, a mass spectrometer, an infrared absorbance detector or the like.

The following examples illustrate the present invention and are not intended to limit the same.

EXAMPLE 1

This example illustrates processes for making the sample concentration columns shown in FIGS. 1 and 2. The capillary types used are fused silica capillaries containing a short length (1–5 mm) of chromatographic packing material in an otherwise empty capillary (total length between 10–100 cm). This chromatographic packing material is placed close to the injection end of the capillary.

Process 1

A fused silica capillary 5 um inner diameter ×60 cm was cut from bulk material using a capillary cleaving tool. One end of the capillary was placed in a manipulator which includes electrodes, with the end of the capillary extending about 1 cm from the electrodes. The other end of the capillary was attached to the axis of a motor, and the capillary was turned between 10–1000 rpm within the manipulator (available from Polymicro Technologies, Phoenix, Arizona) to provide for even heat application. The manipulator was fired 1–4 times for about 10 seconds and a current setting of 25 at each burst. A neck was formed within the capillary at the inner point 14 of capillary as seen in FIG. 1. The inner diameter at the narrowest point was about 10 um. The capillary was then removed from the motor and manipulator. A vacuum was the applied to the opposite end of the capillary, and the end containing the neck was immersed in a suspension of chromatographic particles uBondapak C18 (available from the Waters Division of Millipore, Milford, MA) with a size distribution of 15–20 um. The beads were suspended in methanol. The beads were pulled into the capillary using the force of a vacuum, forming a packed bed that started at the neck and proceeded to the end of the capillary as shown as 18 in FIG. 1. The tube was then removed from the packing suspension and the vacuum was applied until all of the methanol has been removed. The capillary was then returned to the manipulator and another neck (20) was created in the same manner to contain the packing material. The final capillary is seen in FIG. 1. The flow properties of the capillary were then tested by trying to push methanol through the capillary with a Hamilton Gas Tight syringe. If the fluid moved freely, the capillary was ready for use.

Process 2

A fused silica capillary 100 um × 60 cm was cut from bulk material using a capillary cleaving tool. One end of the capillary was pushed into dry glass shot (low melting point borosilicate glass beads) with a particle distribution between 1 and 50 um. This results in a few glass beads entering the tip of the capillary. A metal wire or fused silica fiber with an outer diameter between 75 and 100 um was then inserted into the end of the capillary using a binocular microscope for visualization. The glass beads were pushed into the capillary and concentrated in a small area from 3-5 mm from the end of the capillary. The capillary was then placed in the manipulator so that the cluster of glass beads is between the electrodes. One burst of voltage was then applied for 10 seconds at a current setting of 10 to the capillary. This results in partial melting of the glass beads, so that they fused together to form a porous frit. (See FIG. 2, (28)). The opposite end of the capillary was then attached to a vacuum source and the end containing the frit is immersed in a suspension of C18 coated porous silica beads (Delta Pak C18 available from the Waters Division of Millipore, Milford, MA) with a particle distribution from 15-20 um. The beads were suspended in methanol. This results in the formation of a packed bed of beads beginning at the frit (28) and extending to the end of the capillary. The capillary was then placed under the microscope, and the wire inserted again to Pack the beads further, leaving a 1-2 mm empty space at the end of the capillary. The opposite end of the capillary was then attached to a vacuum source, and the packed end immersed in a suspension in methanol of the same glass shot used before. This results in a final filling of the end of the capillary with glass shot. Finally, the capillary was again placed in the manipulator, with the glass beads at the end of the capillary placed between the electrodes. One burst of voltage was then applied for 10 seconds at a current setting of 10. This results in the formation of a second frit (30) to contain the packing material (18) (See FIG. 2). The capillary was tested for its flow properties using a Hamilton Gas Tight syringe to force methanol through the capillary. If fluid moved freely through the capillary, then it was ready for use.

USE

Samples were loaded into the capillary of FIGS. 1 or 2 using electromigration at 7 kV. Once the sample was loaded onto the beads in the capillary, they were released for separation with the subsequent injection using electromigration at 3 kV of a 60/40 mixture of acetonitrile/running buffer. The running buffer used was 10 mM NaP0$_4$ at pH 7.0. All separations were conducted at 7 kV.

Use 1

Figure 6:
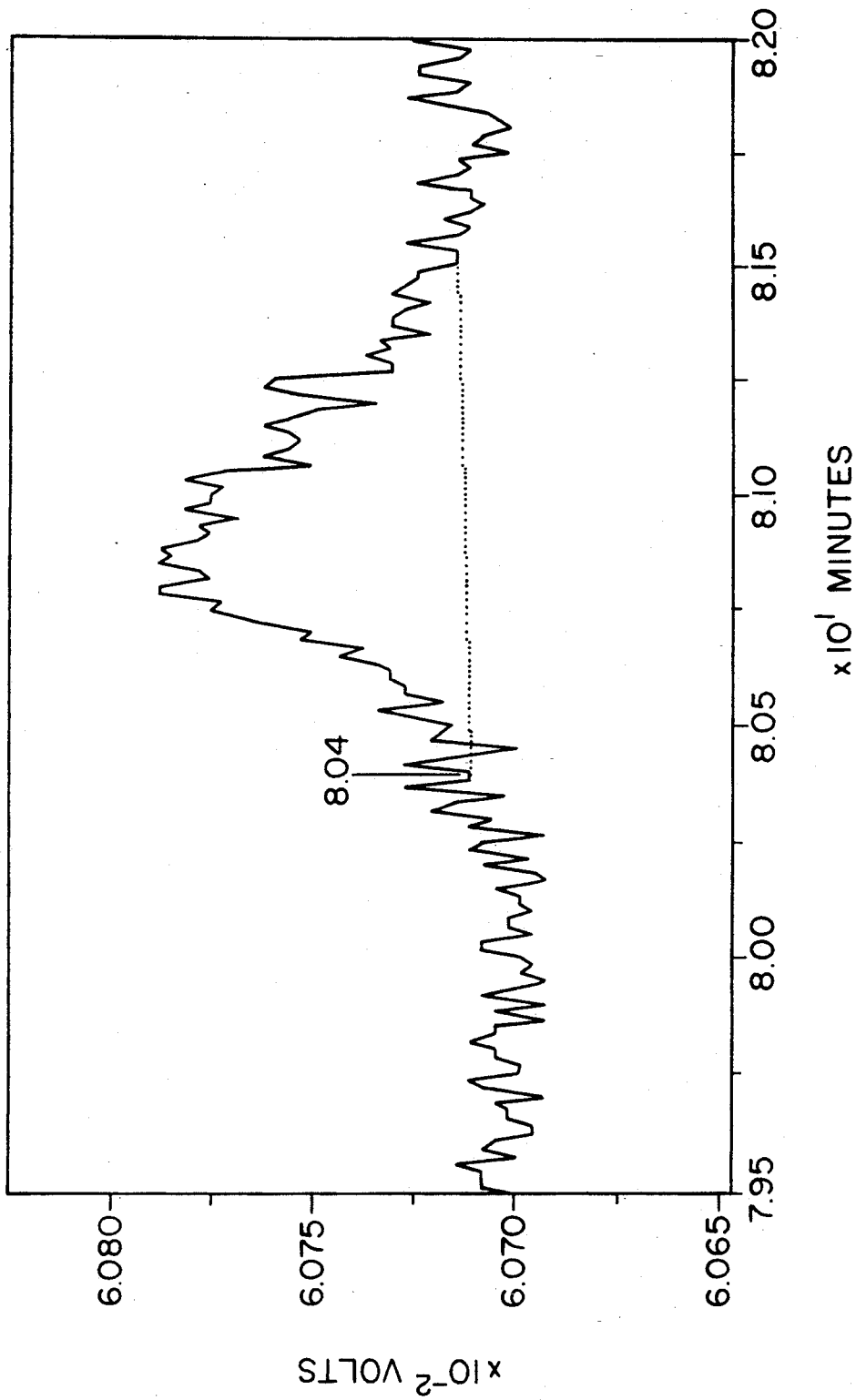
FIG. 6 is an electrophoretogram of a sample obtained by the process of the prior art.

As a reference, the peptide neuromedin is seen in FIG. 6. This was separated using an unmodified fused silica capillary. The limit of detection at 214 nm as demonstrated here is about 1 ug/ml. Smaller concentrations are not detectable using this instrumentation.

Figure 7:
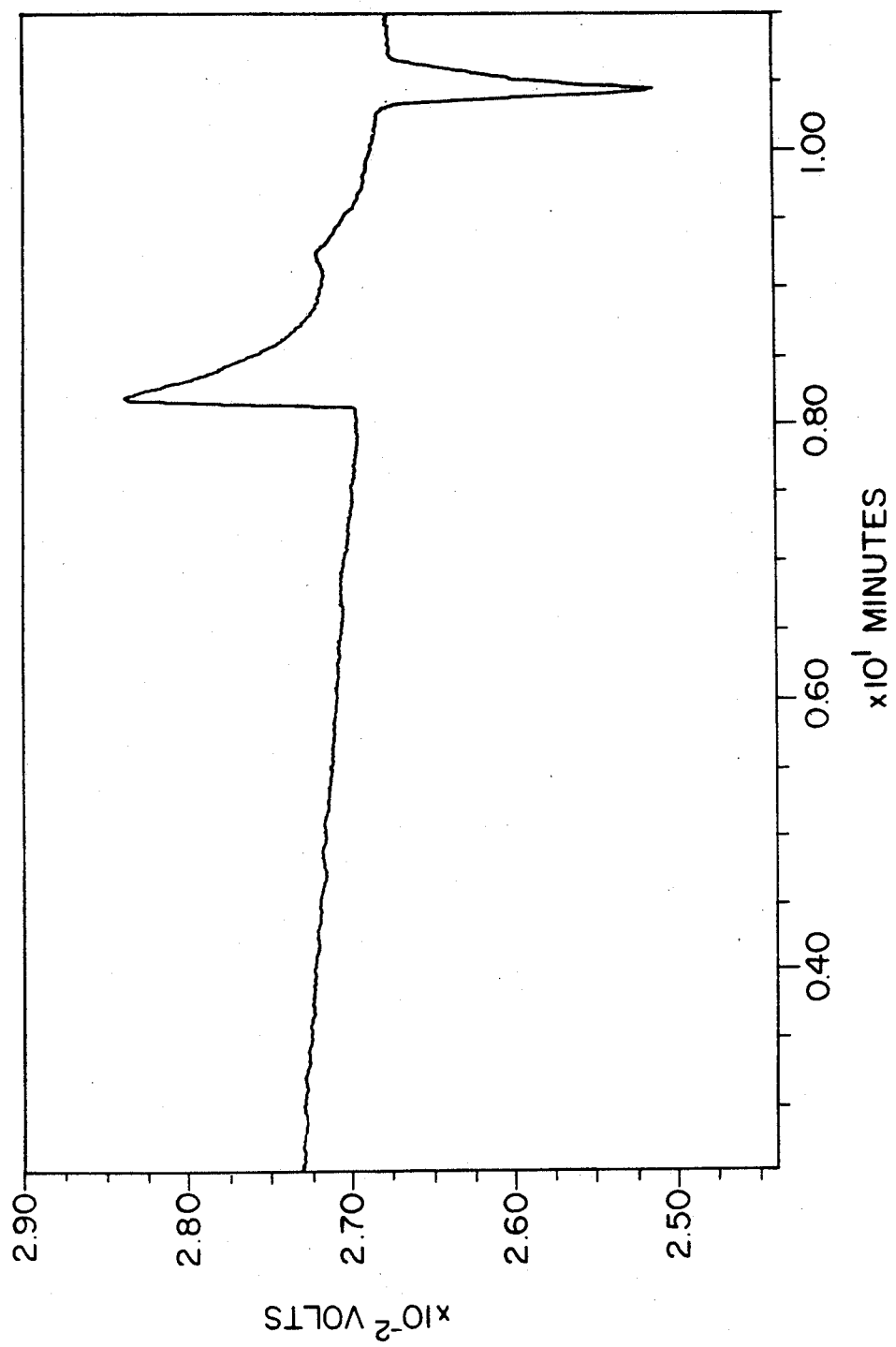
FIG. 7 is an electrophoretogram of the same sample of FIG. 6 but utilizing the process of this invention.

The same peptide is separated using the capillary produced in process 1 and is shown in FIG. 1. The concentration of the sample is again 1 ug/ml. However, it is clear that the limit of sensitivity has been dramatically reduced. This represents about a 50 fold increase in sensitivity as seen in FIG. 7.

Use 2

Figure 8:
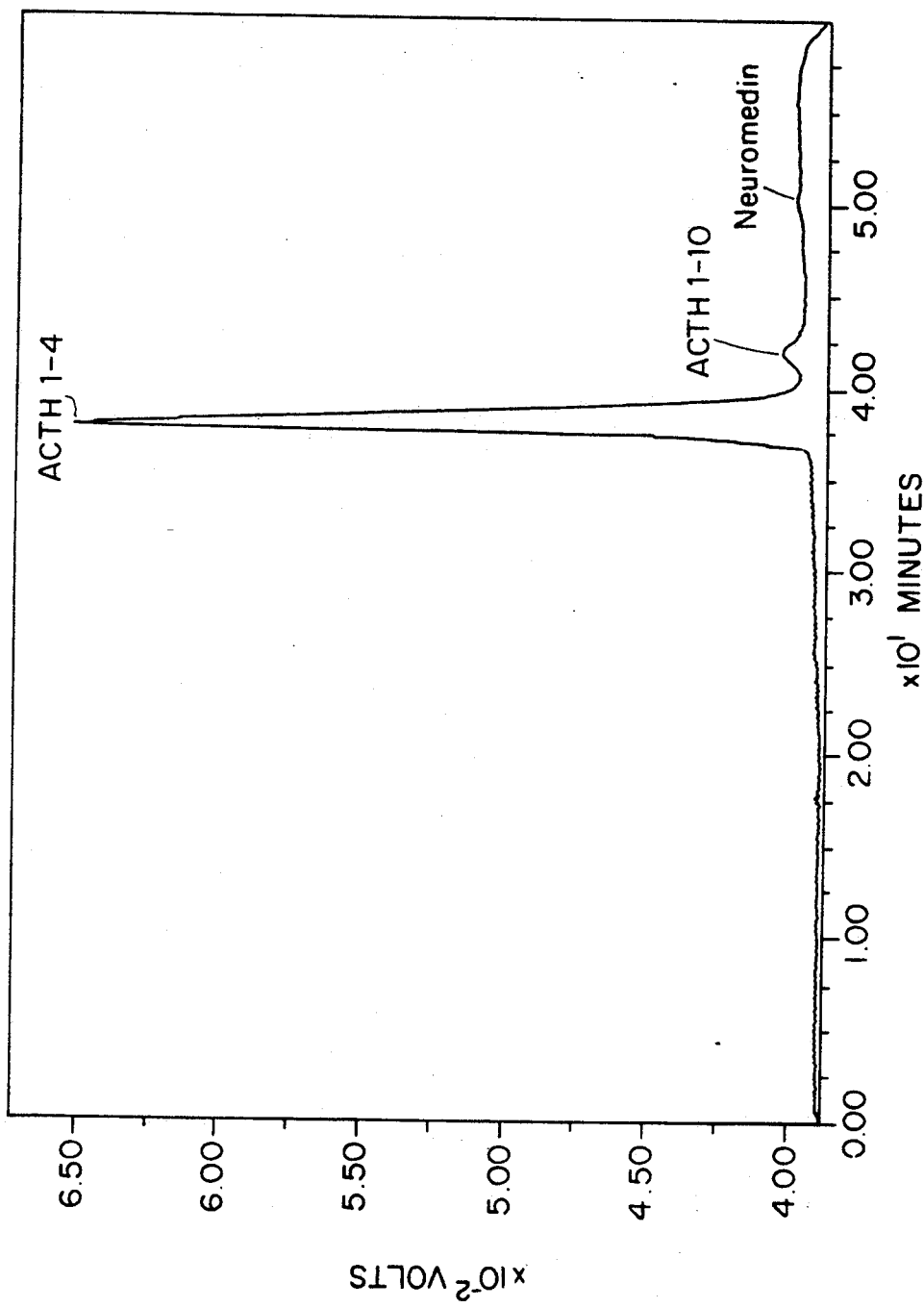
FIG. 8 is an electrophoretogram of the sample processed in Example 2 by the process of the invention.

The peptide ACTH 1-4 at 100 ng/ml is separated using the capillary shown in FIG. 2 produced by process 2. The limit of detection without preconcentration for this peptide is about 1 ug/ml. The estimated increase in sensitivity here is about 400 fold. A mixture of peptides were separated on the capillary produced in Process 2. They were ACTH 1-4 at 1 ug/ml + ACTH 1-10 at 50 ng/ml + Neuromedin at 5 ng/ml. The separation is seen in FIG. 8. This represents about a 400 fold increase in sensitivity.

We claim:

1. Apparatus for conducting a capillary separation process selected from the group consisting of capillary electrophoresis or micellar electrokinetic capillary chromatography which comprises:
    a first capillary tube section comprising a capillary tube having an inner diameter between about 1 and 500 micrometers and containing a packing capable of retaining a solute sample from a first solvent and subsequently releasing said solute sample into a second solvent, said first tube section including means for retaining said packing within said first tube section while permitting fluid flow through said first tube section,
    said first tube section having an inlet an outlet, said outlet being in fluid communication with a capillary tube section,
    a second capillary tube section, having an inner diameter between about 1 and 500 micrometers and free of a packing material.
    a source of a first solvent,
    a source of a second solvent,
    means for introducing said first solvent containing said solute sample into said first tube section,
    means for introducing said second solvent into said first tube section and for introducing said second solvent containing said solute sample into said capillary tube section,
    and means for effecting said capillary separation process in said capillary tube section.
2. The apparatus of claim 1 wherein said packing is a particulate packing.
3. The apparatus of claim 1 wherein said packing is a gel packing.
4. The apparatus of claim 1 wherein said means for retaining comprises two constrictions in said first tube section and wherein said packing is positioned between said constrictions.
5. The apparatus of claim 1 wherein said means for retaining comprises two porous plugs in said first tube section and wherein said packing is positioned between said porous plugs.
6. The apparatus of any one of claims 1, 2, 3, 4, or 5 wherein said first tube section and said capillary tube section are formed integrally.
7. The apparatus of any one of claims 1, 2, 3 4 or 5 herein said first tube section and said capillary tube section are formed separately and are retained in conjunction with each other by a sleeve surrounding said sections.

* * * * *